US00PP12519P2

(12) United States Plant Patent
Olesen et al.

(10) Patent No.: US PP12,519 P2
(45) Date of Patent: Apr. 2, 2002

(54) SHRUB ROSE PLANT NAMED 'POULRIJK'

(76) Inventors: L. Pernille Olesen; Mogens N. Olesen, both of Hillerødvejen 49, DK-3480, Fredensborg (DK)

( * ) Notice: Subject to any disclaimer, the term of this patent is extended or adjusted under 35 U.S.C. 154(b) by 0 days.

(21) Appl. No.: 09/261,445

(22) Filed: Mar. 3, 1999

(51) Int. Cl.[7] ..... A01H 5/00
(52) U.S. Cl. ..... Plt./107
(58) Field of Search ..... Plt./149, 102, 107, Plt./123, 141, 148

(56) References Cited

U.S. PATENT DOCUMENTS

PP9,457 P * 2/1996 Olesen et al. ..... Plt./107

OTHER PUBLICATIONS

UPOV–ROM, 2000/04, Plant Variety Database, GTI Jouve Retrieval Software, 4 citations for 'POULrijk'.*
Copy of NL PBR R002156, filed Aug. 1, 1994.*
Copy of PL PBR ROAO742, granted Feb. 2, 1998 and filed Aug. 31, 1995 (application 0224).*
Copy of DK PBR 15765, granted Jan. 10, 1995.*
Copy of EU 0601/95, filed Aug. 8, 1995 and EU0621 granted Aug. 2, 1996.*

* cited by examiner

*Primary Examiner*—Howard J. Locker

(57) ABSTRACT

A new shrub rose plant which has abundant, non-fading, pink flowers and attractive foliage. This new and distinct variety has shown to be uniform and stable in the resulting generations from asexual propagation.

1 Drawing Sheet

SUMMARY OF THE INVENTION

The present invention constitutes a new and distinct variety of ground cover rose plant which originated from a controlled crossing during summer of 1986 between an unnamed seedling and Dorus Rijkers. The two parents were crossed and the resulting seeds were planted in a controlled environment. The new variety is named 'POULrijk'.

The new rose may be distinguished from its seed parent, an unnamed seedling, by the following combination of characteristics:

1. The seed parent is a low growing, spreading variety and 'POULrijk' is a shrub rose.

2. The seed parent has small, single pink flowers with 5–8 petals and the and 'POULrijk' has larger, double pink flowers with 20–25 petals.

3. The seed parent has small foliage, whereas 'POULrijk' has small to medium foliage.

The new variety may be distinguished from its pollen parent, Dorus Rijkers, by the following combination of characteristics:

1. The pollen parent is a pink floribunda rose, while 'POULrijk' is a shrub rose.

The objective of the hybridization of this rose variety for nursery and landscape use was to create a new and distinct variety with unique qualities, such as:

1. A garden rose plant with abundant, double, pink flowers;

2. Extended period of bloom;

3. Good growth as a traditionally budded plant as well as on its own roots;

4. Glossy thick foliage with excellent disease resistance.

This combination of qualities is not present in previously available commercial cultivars of this type and distinguish 'POULrijk' from all other varieties of which we are aware.

As part of their rose development program, L. Pernille Olesen and Mogens N. Olesen germinated the seeds from the aforementioned hybridization and conducted evaluations on the resulting seedlings in a controlled environment in Fredensborg, Denmark.

'POULrijk' was selected by the inventors in the spring of 1987 as a single plant from the progeny of the aforementioned hybridization. Asexual reproduction of 'POULrijk' by cuttings and traditional budding was first done by L. Pernille and Mogens N. Olesen in their nursery in Fredensborg, Denmark in August, 1992. This initial and other subsequent propagations conducted in controlled environments have demonstrated that the characteristics of 'POULrijk' are true to type and are transmitted from one generation to the next.

BRIEF DESCRIPTION OF THE DRAWING

The accompanying color illustration shows as true as is reasonably possible to obtain in color photographs of this type, the typical characteristics of the buds, flowers, leaves, stems, and a plant of 'POULrijk'. Specifically illustrated in SHEET 1:

1. Stem or entire plant showing branching and the attachment of leaves, buds, and peduncles;

2. Flower bud, partially opened bud, and open bloom;

3. Flower petals, detached;

4. Sepals, receptacle, and pedicel;

5. Flowering stem as well as a bare stem exhibiting thorns;

6. Leaves.

DETAILED DESCRIPTION OF THE VARIETY

The following is a description of 'POULrijk', as observed in September, 1998 in its growth in a field nursery in Jackson County, Oreg. Color references are made using The Royal Horticultural Society (London, England) Colour Chart, 1995, except where common terms of color are used. For a comparison, several physical characteristics of the rose variety 'POULans', a shrub rose variety from the same inventors described and illustrated in U.S. Plant Pat. No. 9,664 and issued on Oct. 22, 1996 are compared to 'POULrijk' in Chart 1.

CHART 1

| | 'POULrijk' | 'POULans' |
|---|---|---|
| Flower bud color when sepals first unfold | Red-Purple Group 58B–C. | Red Group 53C. |
| Petals, upper surface upon opening | Red-Purple 58C–D. | Red-53A–B. |
| Flower bloom diameter when open | 35 mm diameter. | 45–55 mm diameter. |

Parents:
*Seed parent.*—Unnamed, unpatented seedling.
*Pollen parent.*—Dorus Rijkers.
Classification:
*Botanical.*—*Rosa hybrida.*
*Commercial.*—Ground cover rose variety.

FLOWER AND FLOWER BUD

Blooming habit: Recurrent.
Flower bud:
*Size.*—Upon opening, 18 mm–22 mm in length from base of receptacle to end of bud.
*Bud form.*—Pointed ovoid.
*Bud color.*—As sepals unfold, Red-Purple Group 58B–C. Red-Purple Group 58B–C at ¼ opening.
*Sepals.*—Yellow-Green Group 144B. Weak foliaceous appendages on three of the five sepals. Surfaces of sepals generally lacking pubescence. Stipitate glands on margins. Many sepals with strong intonations of Greyed-Purple Group 184B on outerside. Many blooms have a sixth, usually less developed sepal.
*Receptacle.*—Surface: With fine, white hairs. Shape: Urn-shaped. Size: Small. 4 mm (h)×3 mm (w). Color: Yellow-Green Group 146B. Many receptacles with intonations of Greyed-Purple Group 184B.
*Peduncle.*—Surface: With stipitate glands and fine white hairs. Length: 30–35 mm average. Color: Yellow-Green Group 146B–C. Most peduncles with intonations of Greyed-Purple Group 184B. Strength: Strong.
*Borne.*—Multiple. Generally with 50 to 75 or more buds per flowering stem.
Flower bloom:
*Fragrance.*—Light. Fragrance primarily from stipitate glands on peduncle.
*Duration.*—As a cut flower 1 to 2 days. The blooms have a duration on the plant of approximately 3 to 4 days.
*Size.*—Average flower diameter is 35 mm when open.
*Form.*—Double, medium cup-shape. Shape of flower when viewed from the side: Upon opening, upper part: Flattened convex to convex. Upon opening, lower part: Convex. Open flower, upper part: Flat to flattened-convex. Open flower, lower part: Flattened convex.
*Petalage.*—Average range: 20–25 petals under normal conditions with 6–8 petaloids.
Color:
*Upon opening, petals.*—Upper Surface: Red-Purple Group 58C–D. Reverse Side: Red-Purple Group 57D.
*Upon opening, basal petal spots.*—Outer Side: Green-White Group 157D. Inner Side: Green-White Group 157D.
*After opening, petals.*—Upper Surface: Red-Purple Group 62B. Reverse Side: Red-Purple Group 57D.
*Upon opening, basal petal spots.*—Outer Side: Green-White Group 157D. Inner Side: Green-White Group 157D.
General tonality: On open flower Red-Purple Group 58C. No change in the general tonality at the end of the third to fourth day. Afterwards, general tonality is Red-Purple Group 57D–62A–62B.
Petals:
*Petal reflex.*—Petals generally flat.
*Petal edge.*—Ruffled.
*Shape.*—Deltoid.
*Petaloids.*—Present. Quantity: 6–8.
*Thickness.*—Average.
*Arrangement.*—Informal.
Reproductive organs:
*Pollen.*—Color: Yellow-Orange Group 22A. Abundance: Average.
*Anthers.*—Size: Medium. Color, immature: Yellow Group 13C. Color, mature: Greyed-Orange Group 165C to Brown Group 200C. Abundance: Above average.
*Filaments.*—Generally curved inwards. Color: Green-White Group 157D.
*Stigmas.*—Anthers slightly superior to stigmas in position. Color: Green-White Group 157A.
*Styles.*—Color: Green-White Group 157A.
*Hips.*—None observed.

PLANT

Plant growth: Vigorous, upright to bushy. When grown as a budded field grown plant on *R. multiflora* understock, the average height of the plant itself is 80 cm and the average width is 100 cm.
Stems:
*Color.*—Young wood: Yellow-Green Group 144A. Older wood: Yellow-Green Group 146B.
*Prickles.*—Incidence: Moderate. Size/shape: Both small and long thorns. Smaller thorns linear and 2 mm in length. Abundant in some areas of stem, lacking in others. Longer thorns are 6 mm in length. Deeply concave. Color: Greyed-Purple Group 185A.
*Surface.*—Young wood: Smooth. Older wood: Smooth.
Plant foliage: Normal number of leaflets on normal leaves in middle of the stem: 5–7 leaflets. More often 7 leaflets.
*Leaf size.*—Small to medium. 85–95 mm (l)×55–65 mm (w).
*Abundance.*—Average.
*Color.*—Upper Leaf Surface: Green Group 137A to Yellow-Green Group 147A. Lower Leaf Surface: Yellow-Green Group 146B–147C. Juvenile foliage: Upper surface: Yellow-Green Group 146A with intonations of anthocyanin. Lower surface: Yellow-Green Group 137D with intonations of anthocyanin. Anthocyanin intonation: Location: Peduncles, stems, petioles, rachis, prickles, and leaflet margins. Color: Greyed-Purple Group 184B.

Plant leaves and leaflets:

*Stipules.*—Size: 15 mm (l)×4 mm (w). Color: Yellow-Green Group 144B. Presence of stipitate glands: Along the margins and on lower side of stipule.

*Petiole.*—Length: 22 mm. Color: Yellow-Green Group 146B. Underneath: Fine prickles and limited number of stipitate glands. Color: Yellow-Green Group 144B. Margins: Moderate numbers of stipitate glands.

*Rachis.*—Color: Yellow-Green Group 146B. Underneath: Moderate number of small prickles. Color: Yellow-Green Group 144B. Margins: Stipitate glands limited to areas where leaflet joins rachis.

*Leaflet.*—Edge: Finely serrated. Shape: Ovate. Other: Glossy finish. Thick texture.

Disease resistance: Exceptional resistance to mildew, Black spot, and Botrytis under normal growing conditions in Jackson County, Oreg.

Winter hardiness: Winter hardy in Denmark and in Jackson County, Oreg.

We claim:

1. A new and distinct variety of shrub rose, substantially as herein illustrated and described as a distinct and novel rose variety due to its abundant, double pink flowers and attractive foliage, vigorous and compact growth, good growth as a traditionally budded plant as well as on its own roots; glossy thick foliage with excellent disease resistance.

* * * * *

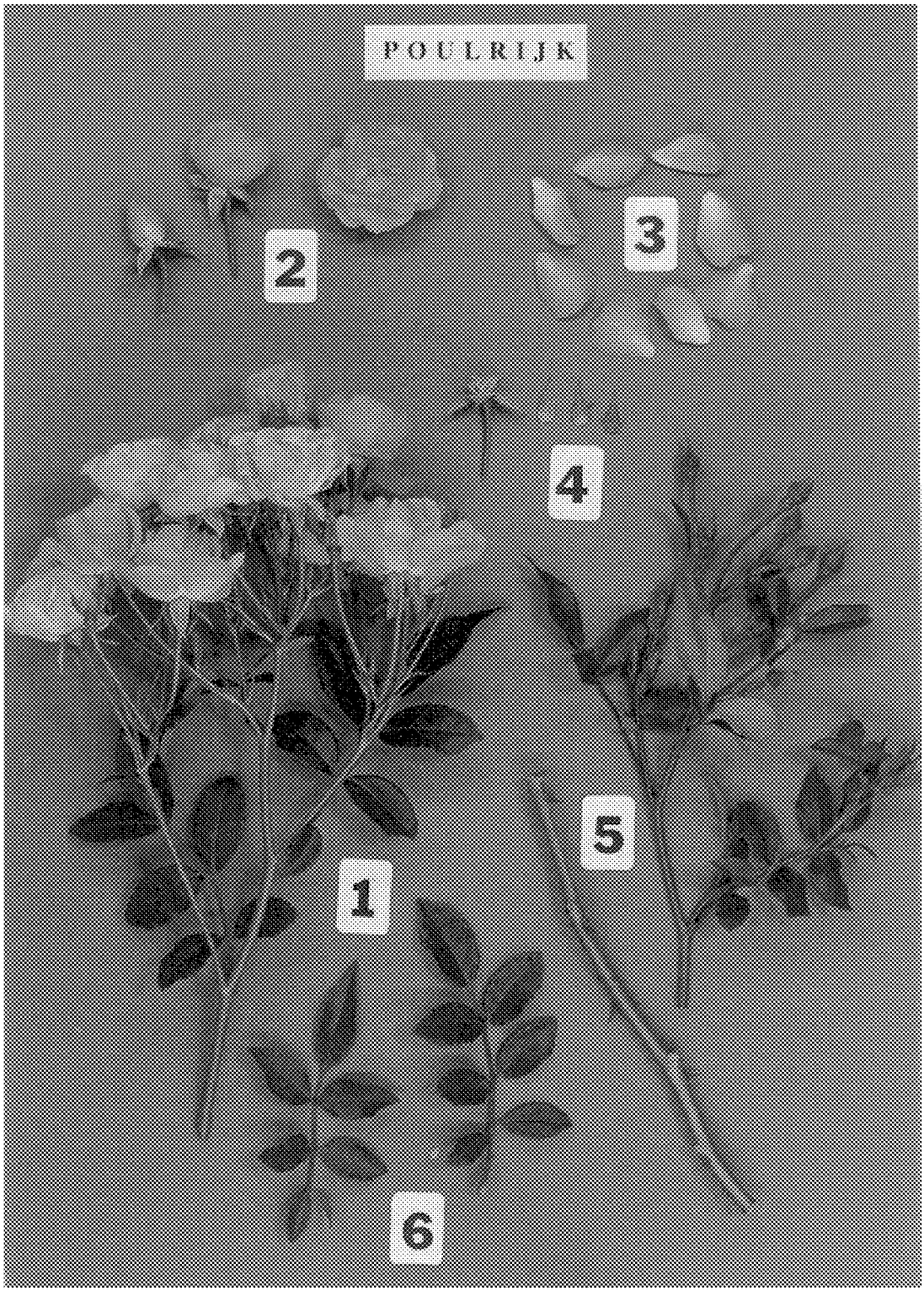
POULRIJK
2
3
4
5
1
6